United States Patent [19]
Bennett et al.

[11] Patent Number: 6,072,106
[45] Date of Patent: *Jun. 6, 2000

[54] SUCROSE ACCUMULATING TOMATO CULTIVAR

[75] Inventors: Alan B. Bennett, Davis, Calif.; Serge Yelle, Quebec, Canada

[73] Assignee: The Regents of the University of California, Oakland, Calif.

[*] Notice: This patent is subject to a terminal disclaimer.

[21] Appl. No.: 08/396,408

[22] Filed: Feb. 28, 1995

Related U.S. Application Data

[63] Continuation of application No. 07/509,673, Apr. 16, 1990, Pat. No. 5,434,344.

[51] Int. Cl.[7] .............................. A01H 1/04; A01H 5/00; A01H 5/08
[52] U.S. Cl. ..................... 800/317.4; 800/263; 800/284
[58] Field of Search ......................... 800/200, DIG. 44, 800/263, 284, 317.4; 47/58; 435/468

[56] References Cited

U.S. PATENT DOCUMENTS 5,434,344  7/1995  Bennett et al. .......................... 800/200

OTHER PUBLICATIONS

Klann et al. 1996. Plant Physiol. 112: 1321–1330.
Tanksley et al. 1988. Theor. Appl. Genet. 75(5): 811–823.
Osborn et al. 1987. Theor. Appl. Genet. 73(3): 350–356.
Yelle et al. 1988. Plant Physiol. 87: 737–740.
Robinson, N.L., "Sink Metabolism in Tomato Fruit," Plant Physiol. 87:727–730 (1988).
Ho, L.C., "Metabolism and Compartmentation of Imported Sugars in Sink Organs in Relation to Sink Strength," Ann. Rev. Physiol.Plant Mol. Biol 39:355–78 (1988).
Prospectus on transgenic plant technology, SIBIA, Sep. 1991.
Rick, C.M., "High Soluble–Solids Content in Large–Fruited Tomato Lines Derived from a Wild Green–Fruited Species," Hilgardia 42:494–509 (1974).
Paterson, A.H., et al., "Resolution of quantitative traits into Mendelian factors by using a complete linkage map of restriction fragment length polymorphisms," Nature 335:721–726 (1988).
Yelle, S., et al., "Selle Metabolism in Tomato Fruit," Plant Physiol. 87:737–740 (1988).
Walker, A.J., et al., "The Tomato Fruit: Import, Growth, Respiration and Carbon Metabolism at Different Fruit Sizes and Temperatures," Ann. Bot. 41:977–985.
Davies, N.J., "Agriculture: Occurrence of Sucrose in the Fruit of Some Species of Lycorpersicon," Nature 209:640–641 (1966).
Manning, K., et al., "Distribution of Acid Invertase in the Tomato Plant," Phytochemistry 14:1965–1969 (1975).
Hewitt, J.D., et al., "Sink Strength of Fruits of Two Tomato Genotypes Differing in Total Fruit Solids Content," J. Amer. Soc. Hort. Soc. 107(5):896–900 (1982).
Yelle, S., et al., "Genetic and Biochemical Analysis of Sucrose Accumulation in Tomato Fruit," Plant Physiology 89 (Supp.):133 (abstract 794, 1989).
Tigchelaar, E.C., "A Tomato Breeding," Breeding Vegetable Crops, A VI Publishing Co., pp. 135–171 (1986).
Poehlman, J.M., "c. The Backross," Breeding Field Crops, Holt, Rinehart and Winston, Inc., N.W. pp. 62–64 (1959).
Robinson, N.L., et al., "Sink Metabolism in Tomato Fruit," Plant Physiol. (1988) 87, 727–730.
Ho, L.C., "Metabolism and Compartmentation of Imported Sugars in Sink Organs in Relation to Sink Strength," Ann. Rev. Plant Physiol. Plant Mol. Biol. (1988) 39: 355–78.
Prospectus on transgenic plant technology, SIBIA, Sep. 1991.
A.J. Walker et al., "Carbon Translocation in the Tomato: Carbon Growth and Fruit Growth," Ann. Bot. 41, 813–823 (1977).
Yelle, S., et al., "Genetic and Biochemical Analysis of Sucrose Accumulation in Tomato Fruit", Plant Physiology, 89 (Supp.) :133 (abstract 794, 1989).

*Primary Examiner*—David T. Fox
*Attorney, Agent, or Firm*—Townsend & Townsend & Crew LLP

[57] ABSTRACT

A new tomato cultivar is provided which is homozygous for a genetically fixable recessive genetic factor which confers the ability to bear fruit that accumulate sucrose. The increased sucrose content, in turn, leads to a higher total soluble solids content in the mature fruit. Higher total soluble solids in tomato fruit are of particular importance to the tomato processing industry. A method for producing the claimed cultivar is also provided.

The claimed genetic factor can be derived from any *Lycopersicon* species which accumulates sucrose in the mature fruit. Once genetically fixed in a tomato cultivar, the factor can be transmitted to other plants in a predictable manner.

11 Claims, No Drawings

SUCROSE ACCUMULATING TOMATO CULTIVAR

This is a continuation of application Ser. No. 07/509,673, filed on Apr. 16, 1990, now U.S. Pat. No. 5,434,344.

BACKGROUND OF THE INVENTION

1. Field of the Invention

The present invention relates generally to the breeding of tomato plants. More specifically, the invention relates to the introduction of a genetic factor that confers on tomato plants the ability to bear mature fruit which accumulate sucrose, thereby increasing the total soluble solids content of the fruit.

2. Information Disclosure

In the prior art, increasing the soluble solids content of tomato fruit has been attempted by introducing the high soluble solids trait from wild *Lycopersicon* species. Rick, *Hilgardia*, 42:494–509 (1974), used *L. chmielewskii* in a breeding plan to produce a variety, known as LA 1563, which showed an increase in soluble solids content. Genetic analysis of this variety indicated that the high soluble solids trait was dominant and was controlled by a number of loci. Restriction fragment length polymorphisms have also been used to create linkage maps of the loci that are associated with the trait. Paterson et al., *Nature*, 335:721–726 (1988).

Investigations of carbohydrate metabolism in tomato reveal that fruit of tomato cultivars accumulate glucose and fructose, but not sucrose. Yelle et al., *Plant Physiol*, 87:737–740 (1988). The rate of carbohydrate import, a determinant of soluble solids content of the tomato fruit, has been reported to be inversely proportional to sucrose concentration in the fruit. Walker and Thornley, *Ann. Bot.*, 41:977–985 (1977).

The fruit of three other *Lycopersicon* species (*L. chmielewskii, L. hirsutum,* and *L. peruvianum*) have been shown to have a high soluble solids content. Accessions of these species accumulate sucrose instead of glucose and fructose. Davies, *Nature*, 209:640–641 (1966). The prior art, however, provided no teaching as to whether this trait was under the control of one or many loci. Studies also show that these species have very low acid invertase level compared to *L. esculentum*. Manning and Maw, *Phytochemistry*, 14:1965–1969 (1975) and Yelle at al., supra. The fruit of the high solids variety produced by Rick, LA 1563, has been shown not to accumulate sucrose. Hewitt et al., *J. Amer. Soc. Hort. Soc.*, 107, 896–900 (1982). This result suggests that the *L. chmielewskii* trait for sucrose accumulation was not genetically fixed in LA 1563.

SUMMARY OF THE INVENTION

The present invention provides a tomato plant which is homozygous for a single, recessive genetic factor which confers on the plant the ability to bear mature fruit which accumulate much more sucrose than hexose sugars. Generally, the sucrose content of the fruit will be between about 20 μmol per gram fresh weight and about 175 μmol per gram fresh weight, preferably from about 50 μmol to about 150 μmol, and most preferably about 100 μmol.

As a result of the increased sucrose the mature fruit of the claimed plant have an increased total soluble solids content. The soluble solids content is generally between about 6% by fresh weight and about 12% by fresh weight, preferably from about 7.5% to about 10%, and most preferably about 8%.

The fruit of the claimed plant have a lower level of invertase activity than standard tomato cultivare. Typically, the invertase activity is less than about 5 μmol of glucose produced per gram of fresh weight in one minute. Invertase activity is preferably less than about 1 μmol and most preferably about 35 nmol.

The genetic factor can be derived from any sucrose accumulating *Lycopersicon* species. It is preferably derived from *L. chmielewskii*.

The invention also provides a method for introducing into a tomato plant a single, recessive genetic factor which confers on the tomato plant the ability to bear a mature fruit having an total soluble solids content of about 8% by fresh weight. The method comprises the steps of crossing the tomato plant with a second plant in the genus *Lycopersicon* having the genetic factor, thereby producing an F1 generation; selfing the F1 plants, thereby producing an $F_2$ generation; selecting $F_2$ plants which produce mature fruit having a sucrose content of about 100 μmol per gram fresh weight; and back-crossing the selected $F_2$ plants with *L. esculentum,* thereby producing a $BC_1F_1$ generation; selfing the $BC_1F_1$ plants, thereby producing a $BC_1F_2$ generation; selecting $BC_1F_2$ plants with the desired phenotype and backcrossing with *L. esculentum* as the recurrent parent until an agromonically useful cultivar is produced. The second plant can be either *L. chmielewskii* or *L. esculentum*. If the second plant is *L. esculentum,* it is typically a tomato cultivar.

The present invention also provides a genetically fixed genetic factor which confers on a tomato plant, the ability to bear a mature fruit which accumulate sucrose in place of hexose sugars. Generally, the sucrose content of the fruit will be between about 20 μmol per gram fresh weight and about 175 μmol per gram fresh weight, preferably about 100 μmol.

The mature fruit of a plant expressing the claimed factor exhibit an increased total soluble solids content. The soluble solids content is generally between about 6% by fresh weight and about 12% by fresh weight, preferably about 8%.

The fruit of the plant expressing the claimed factor have a lower level of invertase activity than standard tomato cultivars. Typically, the invertase activity is less than about 5 μmol of glucose produced per gram of fresh weight per minute.

The genetic factor can be derived from any sucrose accumulating *Lycopersicon* species. It is preferably deprived from *L. chmielewskii*.

The present invention also provides tomato seed homozygous for the genetic factor. Plants derived from the seed have a sucrose content from about 20 μmol per gram fresh weight to about 175 μmol per gram fresh weight. The plants derived from the seed also exhibit increased total soluble solids and decreased invertase activity in the mature fruit.

DETAILED DESCRIPTION OF THE INVENTION

Improved tomato plants (*Lycopersicon esculentum*) characterized by a genetically fixable and recessive genetic factor which confers the ability to bear fruit having an increased total soluble solids are provided. The genetic factor is derived from *Lycopersicon* species which accumulate sucrose in the mature fruit. The genetic factor acts substantially as a recessive gene or locus which can be transmitted between tomato cultivars by conventional breeding techniques.

Soluble solids are of major economic significance to the tomato processing industry. For example, tomato paste must contain at least 24% soluble solids. Standard tomato cultivars, however, generally have a total soluble solids content of between 5 and 7%. Hewitt and Garriay, in *Tomato Biotechnology*, pp. 45–54 (Nevins and Jones, eds. 1987). It is estimated that a savings of $7 million can be realized by the tomato processing industry for every 0.1% increase in soluble solids content. Kunimoto, *Food Tech.*, pp. 58–60 (October, 1986).

While not wishing to be bound by theory, increased total soluble solids content in the fruit of tomato plants expressing the claimed genetic factor apparently results from increased accumulation of sucrose in the mature fruit. Sucrose accumulation is apparently the result of decreased activity of the enzyme, acid invertase, which catalyzes the hydrolysis of sucrose to glucose and fructose. Thus, sucrose, rather than glucose and fructose, accumulates in the fruit of plants expressing the claimed genetic factor. Sucrose accumulation presumably leads to higher total soluble solids for two reasons. First, sucrose is not as readily metabolized as glucose and fructose. Unless sucrose is cleaved, it is stored as a metabolic end product and is not consumed through respiration. Second, because sucrose is a disaccharide, twice as much sucrose as glucose and fructose can accumulate, while maintaining the same turgor pressure.

The method of the present invention is not limited to the particular factor which has been isolated. Any *Lycopersicon* species which accumulates sucrose in the mature fruit can be the source of the claimed genetic factor. The genetic factor isolated from *L. chmielewskii* is preferred because crosses between that species and tomato cultivars can be readily made. Other species that could be used as a source for the claimed genetic factor include *L. hirsutum, L. hirsutum* var. *glabratum,* and *L. peruvianum.*

The methods of the present invention can be used to modify and improve the soluble solid content of all tomato cultivars. Open pollinated cultivars that can be used include Hunt 100, UC204, E6203, UC82B, Advantage, and HM3075. Hybrid cultivars that can be used include, FM785, Alta, Lassen, Brigade, N1400, N1401 and N1200.

The method of the present invention can be used to produce tomato cultivars for commercial tomato production. Any standard method used for crossing tomato plants can be used. Generally, the methods involve emasculation of one parent, followed by application of pollen from the other parent to the stigma of the first parent. The crosses can be performed using either parent as the pollen parent. Embryo rescue can also be performed if the flowers abort after pollination.

A tomato plant of the present invention can be obtained by crossing a plant homozygous for the claimed genetic factor with any tomato cultivar lacking the factor. The plant containing the factor can be any *Lycopersicon* species, including a tomato cultivar in which the factor has been previously genetically fixed.

Because the genetic factor is recessive, the $F_1$ generation will not accumulate sucrose in the mature fruit. Only a tomato plant homozygous for the genetic factor will exhibit the sucrose-accumulating phenotype. This phenotype can be used to identify progeny that are homozygous for the claimed genetic factor.

After selfing the $F_1$ population, the $F_2$ generation will exhibit the phenotype in a ratio of approximately 1:4. Back-crossing $F_2$ sucrose-accumulating individuals with *L. esculentum* plants will produce the $BC_1F_1$ population. Selfing the $BC_1F_1$ population will give the $BC_1F_2$ generation. As in the $F_2$ population, the sucrose-accumulating trait will segregate in a ratio of about 1:4 in this population. Repeated back-crosses will produce a sucrose-accumulating tomato cultivar with the characteristics of the recurrent, parent cultivar. The claimed genetic factor will thus become generally fixed in the resulting cultivar. The trait may then be transmitted by sexual crossing to other cultivars, if desired.

Of course, other breeding schemes can be used to introduce the genetic factor into the desired cultivar. The particular scheme used is not critical to the invention, so long as the genetic factor is stably incorporated into the genome of the cultivar. For instance, other marker genes such as TG102, which is associated with sterility of flowers in crosses between *L. esculentum* and *L. chmielewskii*, can be used. TG102 is apparently tightly linked to the claimed genetic factor (see experimental section, infra). A nucleic acid probe which hybridizes to the TG102 market gene can be used to identify the desired plants in the $F_1$ generation. This approach would eliminate the need for selfing the progeny of each backcross.

In order to determine if a cultivar possesses the claimed genetic factor, a classic genetic test for allelism can be performed. The cultivar is crossed with a plant known to possess the claimed genetic factor and to exhibit the sucrose accumulating phenotype. By analyzing the resulting $F_1$ generation, the genotype of the unknown cultivar can be determined. If the unknown cultivar possesses the genetic factor, the sucrose-accumulating phenotype will be observed in the $F_1$ generation. Nonallelic genetic factors that also result in sucrose accumulation can be identified by analyzing the sugar composition of the unknown cultivar.

A tomato plant having the high soluble solids phenotype can be characterized by its ability to transmit the phenotype to progeny when crossed with a normal tomato cultivar that lacks the claimed genetic factor. In addition, plants with the high soluble solids phenotype will display certain well defined characteristics. First, the fruit will have total soluble solids content of about 8%. Total soluble solids are typically measured as °Brix. °Brix is a standard refractometric measure of soluble solids which primarily detects reducing sugars, but is also affected by other soluble constituents. 1° Brix is approximately 1% by weight.

Second, the fruit will accumulate much more sucrose than hexose sugars and have a sucrose content of about 100 μmol per gram fresh weight. The sugar content of the fruit is typically determined using the arsenomolybdate based assay for reducing sugars described in Nelson, *J. Biol. Chem.*, 153:375–380 (1944) which is incorporated herein by reference. Sucrose content can be determined by the difference in values obtained from samples incubated in the presence and absence of invertase.

Third, the acid invertase levels in the fruit will be low, generally about 35 nmol of glucose produced per gram of fresh weight in one minutes. Enzyme activities are typically determined by the method of Robinson et al., *Plant Physiol.*, 87:727–730 (1988), which is incorporated herein by reference. According to this method, endogenous hexose sugars are removed form crude extracts of tomato fruit. The samples are incubated for 30 minutes and the reducing sugars produced are measured using the assay of Nelson, supra.

DEFINITIONS

The phrase "total soluble solids" refers to the soluble portion of the dry matter of *Lycopersicon* fruit. The soluble solids are composed of carbohydrates, the major components of which are starch and sugars. In *Lycopersicon* fruit, the sugars are primarily the hexoses, fructose and glucose, and the disaccharide, sucrose.

The term "recessive" is used to refer to an allele whose phenotypic effect is masked in a heterozygote by another, dominant, allele. Thus, the heterozygote is indistinguishable phenotypically from individuals homozygous for the dominant allele.

The term "homozygous" refers to condition in which a diploid individual carries identical alleles at a given genetic locus.

The term "genetic factor" refers to a genetic locus flanked by at least one non-wild type region which is stably incorporated into the genome of a plant and which confers on the plant a characteristic phenotype.

The term "fresh weight" refers to the total weight of plant tissue, it includes both dry matter and wafer.

The term "mature fruit" refers to fully ripe tomato fruit with a total lycopene content (the primary pigment in ripe fruit) of about 40–70 μgrams per gram fresh weight. Maturity is typically reached about 40 to 50 days after anthesis.

The term "cultivar" refers to a commercially valuable, horticulturally derived, variety, as distinguished from a naturally occurring variety.

The term "genetically fixed" refers to a genetic factor which has been stably incorporated into the genome of a plant that normally does not contain the genetic factor. When genetically fixed, the genetic factor can be transmitted in a predictable manner to other plants by sexual crosses.

The term "sucrose-accumulating" refers to a phenotype characterized by the ability of the mature fruit to accumulate much more sucrose than hexose sugars.

The following experimental results are offered by way of example and not by way of limitation.

EXAMPLES

I. Segregation of Sucrose-Accumulating Trait

*L. esculentum* cv. UC 82 (available from Department of Vegetable Crops, University of California, Davis) and *L. chmielewskii* (LA 1028, available from the Tomato Genetic Stock Center, University of California, Davis) were crossed using standard methods of pollination and emasculation. The resulting $F_1$ hybrids were selfed to yield a population of $F_2$ progeny that were analyzed for sugar composition.

For sugar determination, 3 g of ripe fruit tissue was homogenized in 80% ethanol and heated to 100° C. for 20 minutes and centrifuged to remove insoluble material. Replicate samples were analyzed for reducing sugars using the arsenomolybdate based assay of Nelson, supra. Sucrose concentration was determined by incubating the sugars of each sample in the presence of yeast invertase at 37° C. for 30 minutes. (Yeast invertase was obtained from Sigma Chemical Co., St. Louis, Mo.). Sucrose content was then inferred by comparing the sugar concentration of samples in the presence and absence of invertase. The raw data for sucrose concentration obtained by this method were expressed in equivalent glucose concentration (μmol/gr fr wt). Because sucrose is a disaccharide, the actual sucrose concentration in each fruit is one-half the value obtained.

In the $F_2$ population, 6 of 91 plants analyzed bore fruit that accumulated sucrose as the predominant sugar. A sucrose accumulating plant was backcrossed with *L. esculentum* cv. UC 204B (available from Department of Vegetable Crops, University of California, Davis). This cross produced a population of $BC_1F_1$ progeny which were selfed to produce the $BC_1F_2$ population that was again analyzed for sugar composition. UC 204B was used as the recurrent parent in all subsequent backcrosses.

Analysis of sugar composition of the $BC_1F_2$ population gave the results as summarized in Table 1.

TABLE I

Sugar composition of $BC_1F_2$ fruit and UC82.

| Population | Hexose μmol/gr fr wt | Sucrose μmol/gr fr wt | Total Sugar μmol/gr fr wt |
|---|---|---|---|
| UC82 N = 46 | 165.9 | 6.4 | 178.7 |
| $BC_1F_2$ (Sucrose Accumulators) | | | |
| 4005-4 | 19.2 | 168.9 | 326.9 |
| 4005-5 | 38.2 | 97.4 | 232.9 |
| 4079-5 | 48.4 | 107.8 | 263.9 |
| 4077-13 | 55.7 | 86.1 | 227.8 |
| 4006-27 | 69.0 | 81.5 | 232.0 |
| 4005-1 | 83.8 | 84.4 | 252.6 |
| 4077-7 | 83.3 | 55.6 | 194.4 |
| 4077-6 | 83.8 | 51.4 | 186.5 |
| 4079-7 | 120.3 | 70.0 | 260.2 |
| 4006-18 | 117.1 | 37.2 | 191.4 |
| X̄ | 71.9 | 82.5 | 236.9 |

Total Sugar content expressed as equivalent glucose units.

The ratio of sucrose to hexose-accumulating plants in the $BC_1F_2$ population was 1:5.6 (10 plants out of 56), rather than the predicted 1:4 for a trait determined by a single, recessive gene. Restriction fragment length polymorphisms were utilized to map the chromosomal location of the genetic factor conferring sucrose accumulation and found to be localized adjacent to a DNA marker, TG102, on chromosome 3. This region is also associated with sterility of flowers in crosses between *Lycopersicon esculentum* and *Lycopersicon chmielewskii*. It was found that six $BC_1F_2$ plants scored as homozygous for the *L. chmielewskii* allele of TG102. These plants were sterile and thus excluded from analysis although they were likely to be sucrose-accumulators. This consideration suggests that the true ratio of sucrose accumulating plants would have been 1:3.87, consistent with genetic control by a single recessive gene. Because the gene is tightly linked to TG102, the proportion of plants exhibiting the phenotype was artificially reduced.

II. Determination of Total Soluble Solids Content

Total soluble solids content was measured as °Brix. An extract for measuring soluble solids was prepared by mechanically homogenizing fruit and filtering the homogenate through cheesecloth. The refractive index of the filtrate was then determined using a Bausch & Lomb refractometer. The results are presented below in Table II.

TABLE II

Total Soluble Solids in $BC_1F_2$ fruit and UC 82.

| Plant | °Brix |
|---|---|
| UC82 | 5 |
| $BC_1F2_1$ | |
| (Sucrose accumulators) | |
| 4005-4 | 10.8 |
| 4005-5 | N.D. |
| 4079-5 | 10.2 |
| 4077-13 | 8.6 |
| 4006-27 | N.D. |
| 4005-1 | 9.0 |
| 4077-7 | 8.2 |
| 4077-6 | 7.5 |

TABLE II-continued

Total Soluble Solids in BC$_1$F$_2$ fruit and UC 82.

| Plant | °Brix |
|---|---|
| 4079-7 | 7.9 |
| 4006-18 | N.D. |
| Average | 8.9 |

III. Determination of Invertase and Sucrose Synthase Activities

Activities of two enzymes potentially involved in sucrose breakdown were assayed and it was determined that invertase was absent in sucrose accumulating plants but present at high levels in hexose-accumulating tomato fruit.

Invertase and sucrose synthase activities were determined according to the method of Robinson, et al. supra. Briefly, crude extracts from tomato fruit were centrifuged through a 1 ml column of Sephadex G-50 to remove endogenous sugars. The column was washed twice with to 50 mM Hepes-KOH (pH 8.3), followed by two washes with 50 mM Hepes-KOH (pH 8.3) containing 0.1% BSA.

Invertase activity was determined in an assay containing 0.1 ml 6% sucrose in 1 M Na acetate (pH 4.5) and desalted extract in a final volume of 0.2 ml. The reaction was terminated by heat denaturation after 30 minutes at 37° C. The products were determined using the assay of Nelson, supra.

The sucrose synthase assay contained 0.25 μmol UDP [$^{14}$C] glucose (160,000–240,000 cpm/μmol) 0.5 μmol fructose, 5 μmol Tris-HCl (pH 8.0), and desalted extract in a final volume of 0.05 ml. The reaction was terminated after 20 minutes at 30° C. Dowex-1 formate was used to bind unreacted UDP[$^{14}$C] glucose and [$^{14}$C] sucrose was measured by standard methods.

The results of these assays are presented below in Table III.

TABLE III

Invertase and sucrose synthase activities in BC$_1$F$_2$ fruit and UC82 fruit.

| Population | Days after anthesis (days) | Invertase activity (nmol/gr fr wt min) | Sucrose Synthase activity (nmol/gr fr wt min) |
|---|---|---|---|
| UC82 | 20 | 3216 ± 271 | 397 ± 52 |
| N = 46 | 40 | 12839 ± 572 | N.D.* |
| BC$_1$F$_2$ | 20 | 42 ± 20 | 346 ± 57 |
| N = 10 | 40 | 32 ± 29 | N.D.* |

*Sucrose synthase levels not determined (N.D.) at 40 days after anthesis since levels are very low in both *L. esculentum* and *L. chmielewskii* at this developmental stage.

What is claimed is:

1. A *Lycopersicon esculentum* plant which bears mature fruit having a level of invertase activity which is less than about 5 μmol of glucose produced per gram of fresh weight per minute and a sucrose content from about 20 μmol per gram fresh weight to about 175 μmol per gram fresh weight and an increased total soluble solids content wherein said increased total soluble solids content is a result of the lower level of invertase activity.

2. The plant of claim 1, wherein the mature fruit have a soluble solids content of between about 7.5% and about 10% fresh weight.

3. The plant of claim 1, wherein the mature fruit halve a sucrose content from about 50 μmol per gram fresh weight to about 150 μmol per gram fresh weight.

4. A *Lycopersicon esculentum* fruit having:

a lower level of invertase activity than a standard plant cultivar where said lower level of invertase activity is less than about 5 μmol of glucose produced per gram of fresh weight per minute;

a sucrose content from about 20 μmol per gram fresh weight to about 175 μmol per gram fresh weight; and an increased total soluble solids content wherein said increased total soluble solids content is a result of the lower level of invertase activity.

5. The fruit of claim 4, which has a soluble solids content of between about 7.5% and about 10% fresh weight.

6. A method of producing a *Lycopersicon esculentum* plant which bears mature fruit having increased soluble solids, the method comprising introducing a genetic factor into a parent *Lycopersicon esculentum* plant, wherein the genetic factor confers on a plant the ability to bear mature fruit having an acid invertase activity which is less than about 5 μmol of glucose produced per gram fresh weight per minute; and selecting progeny bearing mature fruit having a soluble solids content greater than the soluble solids content of the mature fruit of the parent plant;

wherein the greater soluble solids content in the mature fruit of the selected progeny compared to in the mature fruit of the parent plant is a result of an increased sucrose level in the fruit.

7. The method of claim 6, wherein the step of introducing the genetic factor into the parent tomato plant is carried out by a sexual cross.

8. The method of claim 6, wherein the genetic factor is derived from *Lycopersicon chmielewskii*.

9. The method of claim 6, wherein the selected progeny bear mature fruit having a total soluble solids content from about 6% by fresh weight to about 12% by fresh weight.

10. The plant of claim 1, wherein the mature fruit have a soluble solids content of between about 6% and about 12% fresh weight.

11. The fruit of claim 4, which has a soluble solids content of between about 6% and about 12% fresh weight.

* * * * *